United States Patent [19]

Schwark et al.

[11] Patent Number: 5,559,153
[45] Date of Patent: Sep. 24, 1996

[54] UREA-SUBSTITUTED BENZOYLGUANIDINES, PROCESS FOR THEIR PREPARATION, THEIR USE AS PHARMACEUTICAL OR DIAGNOSTIC, AND PHARMACEUTICAL CONTAINING THEM

[75] Inventors: Jan-Robert Schwark, Frankfurt; Hans-Jochen Lang, Hofheim; Heinz-Werner Kleemann, Bad Homburg; Andreas Weichert, Egelsbach; Wolfgang Scholz, Eschborn; Udo Albus, Florstadt, all of Germany

[73] Assignee: Hoechst Aktiengesellschaft, Frankfurt am Main, Germany

[21] Appl. No.: 289,674

[22] Filed: Aug. 11, 1994

[30] Foreign Application Priority Data

Aug. 13, 1993 [DE] Germany .................... 43 27 244.4

[51] Int. Cl.$^6$ .................. A61K 31/16; A61K 31/535; A61K 31/40; A61K 31/445
[52] U.S. Cl. .................. 514/597; 514/255; 514/237.5; 514/330; 514/423; 514/586; 544/160; 544/168; 544/169; 544/390; 546/226; 548/538; 564/27; 564/51
[58] Field of Search .................. 514/255, 237.5, 514/330, 423, 586, 597; 544/160, 168, 169, 390; 546/226; 548/538; 564/27, 51

[56] References Cited

U.S. PATENT DOCUMENTS

| 3,780,027 | 12/1973 | Cragoe, Jr. et al. .................. 260/239.6 |
| 4,024,183 | 5/1977 | Swallow .................. 564/51 |
| 5,091,394 | 2/1992 | Englert et al. .................. 514/331 |
| 5,292,755 | 3/1994 | Englert et al. .................. 514/331 |

FOREIGN PATENT DOCUMENTS

| 0416499A2 | 3/1991 | European Pat. Off. . |
| 0566674A1 | 8/1993 | European Pat. Off. . |
| 0556674 | 8/1993 | European Pat. Off. . |

Primary Examiner—Peter O'Sullivan
Attorney, Agent, or Firm—Finnegan, Henderson, Farabow, Garrett & Dunner, L.L.P.

[57] ABSTRACT

Urea-substituted benzoylguanidines, process for their preparation, their use as pharmaceutical or diagnostic, and pharmaceutical containing them There are described benzoylguanidines of the formula I

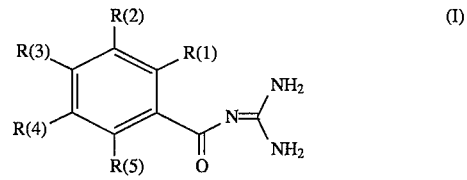

where R(1), R(3) or R(4) is —NR(6) C=X NR(7)R(8); X is oxygen, sulfur, R(6), R(7) and R(8) are H, (perfluoro)alk(en)yl, where R(7) and R(8) can also together be 4 or 5 methylene groups,
the substituents R(1) to R(5) remaining in each case are H, Hal, (fluoro) alk(en)yl, CN, NO$_2$, NR(16)R(17).
On account of their pharmacological properties, the compounds are outstandingly suitable for use as anti-arrhythmic pharmaceuticals having a cardioprotective component for the prophylaxis and treatment of infarction as well as for the treatment of angina pectoris, the compounds also inhibiting or strongly reducing, in a preventive manner, the pathophysiological processes in association with the occurrence of ischemically induced damage, in particular in association with the elicitation of ischemically induced cardiac arrhythmias.
They are obtained by reacting a compound of the formula II.

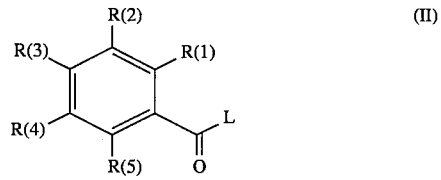

in which L is a leaving group which can readily be substituted nucleophilically, with guanidine.

19 Claims, No Drawings

UREA-SUBSTITUTED BENZOYLGUANIDINES, PROCESS FOR THEIR PREPARATION, THEIR USE AS PHARMACEUTICAL OR DIAGNOSTIC, AND PHARMACEUTICAL CONTAINING THEM

DESCRIPTION

Urea-substituted benzoylguanidines, process for their preparation, their use as pharmaceutical or diagnostic, and pharmaceutical containing them.

The invention relates to benzoylguanidines of the formula I

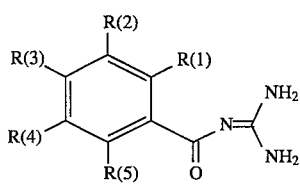

in which:

R(1), R(3) or R(4) is —NR(6) C=X NR(7)R(8),

X is oxygen, S,

R(6) is hydrogen, $(C_1-C_8)$-alkyl, $(C_1-C_8)$-perfluoroalkyl, $(C_3-C_8)$-alkenyl, —$C_nH_{2n}$—R(9), n is zero, 1, 2, 3 or 4, R(9) is $(C_3-C_8)$ -cycloalkyl, phenyl, biphenylyl or naphthyl, where the aromatic systems are unsubstituted or substituted by 1–3 substituents from the group consisting of F, Cl, $CF_3$, methyl, methoxy and NR(10)R(11), R(10) and R(11) are H, $(C_1-C_4)$-alkyl or $(C_1-C_4)$-perfluoroalkyl;

R(7) is hydrogen, $(C_1-C_8)$-alkyl, $(C_1-C_8)$-perfluoroalkyl, $(C_3-C_8)$-alkenyl, —$C_oH_{2o}$—R(12), o is zero, 1, 2, 3 or 4, R(12) is $(C_3-C_8)$ -cycloalkyl, phenyl, biphenylyl or naphthyl, where the aromatic systems are unsubstituted or substituted by 1–3 substituents from the group consisting of F, Cl, $CF_3$, methyl, methoxy and NR(13)R(14), R(13) and R(14) are H, $(C_1-C_4)$-alkyl or $(C_1-C_4)$-perfluoroalkyl;

R(8) is defined as R(7);

where R(7) and R(8) can also together be 4 or 5 methylene groups, of which one $CH_2$ group can be replaced by oxygen, S, NH, N—$CH_3$ or N-benzyl;

the substituents R(2), R(3), R(4), R(5) or R(1), R(2), R(4), R(5) or R(1), R(2), R(3), R(5) remaining in each case are independently of one another hydrogen, F, Cl, Br, I, —$O_{ta}(C_1-C_8)$-alkyl,
—$O_{tb}(C_3-C_8)$-alkenyl
—$O_{tc}(CH_2)_bC_dF_{2d+1}$, —$O_{td}C_pH_{2p}R(18)$,
or up to 2 groups CN, $NO_2$, NR(16)R(17), b is zero or 1, d is 1, 2, 3, 4, 5, 6 or 7, ta is zero or 1, tb is zero or 1, tc is zero or 1, td is zero or 1, p is zero, 1, 2, 3 or 4, R(18) is $(C_3-C_8)$-cycloalkyl, phenyl, biphenylyl or naphthyl, where the aromatic systems are unsubstituted or substituted by 1–3 substituents from the group consisting of F, Cl, $CF_3$, methyl, methoxy and NR(19)R(20), R(19) and R(20) are hydrogen, $(C_1-C_4)$-alkyl, $(C_1-C_4)$-perfluoroalkyl, R(16) is hydrogen, $(C_1-C_8)$-alkyl, $(C_1-C_8)$-perfluoroalkyl, $(C_3-C_8)$-alkenyl, —$C_qH_{2q}$—R(21), q is zero, 1, 2, 3 or 4, R(21) is $(C_3-C_8)$-cycloalkyl, phenyl, biphenylyl or naphthyl, where the aromatic systems are unsubstituted or substituted by 1–3 substituents from the group consisting of F, Cl, $CF_3$, methyl, methoxy and NR(22)R(23), R(22) and R(23) are hydrogen, $(C_1-C_4)$-alkyl or $(C_1-C_4)$-perfluoroalkyl, R(17) is hydrogen, $(C_1-C_8)$-alkyl, $(C_1-C_8)$-perfluoroalkyl, $(C_3-C_8)$-alkenyl, —$C_rH_{2r}$—R(24), r is zero, 1, 2, 3 or 4, R(24) is $(C_3-C_8)$-cycloalkyl, phenyl, biphenylyl or naphthyl, where the aromatic systems are unsubstituted or substituted by 1–3 substituents from the group consisting of F, Cl, $CF_3$, methyl, methoxy and NR(25) R(26), R(25) and R(26) are hydrogen, $(C_1-C_4)$-alkyl or $(C_1-C_4)$-perfluoroalkyl;

where R(16) and R(17) can also together be 4 or 5 methylene groups, of which one $CH_2$ group can be replaced by oxygen, S, NH, N-$CH_3$ or N-benzyl.

Compounds of the formula I are preferred in which:

R(1), R(3) or R(4) is —NR(6) C=X NR(7)R(8),

X is oxygen, S,

R(6) is hydrogen, $(C_1-C_8)$-alkyl, $(C_1-C_8)$-perfluoroalkyl, $(C_3-C_8)$-alkenyl, —$C_nH_{2n}$—R(9), n is zero or 1, R(9) is $(C_3-C_8)$-cycloalkyl, phenyl, which is unsubstituted or substituted by 1–3 substituents from the group consisting of F, Cl, $CF_3$, methyl, methoxy and NR(10) R(11), R(10) and R(11) are H, $CH_3$, R(7) is hydrogen, $(C_1-C_8)$-alkyl, $(C_1-C_8)$-perfluoroalkyl, $(C_3-C_8)$-alkenyl, —$C_oH_{2o}$—R(12), o is zero or 1;

R(12) is $(C_3-C_8)$-cycloalkyl, phenyl, which is unsubstituted or substituted by 1–3 substituents from the group consisting of F, Cl, $CF_3$, methyl, methoxy and NR(13) R(14), R(13) and R(14) are H, $CH_3$, R(8) is defined as R(7), where R(7) and R(8) can also together be 4 or 5 methylene groups, of which one $CH_2$ group can be replaced by oxygen, S, NH, N—$CH_3$ or N-benzyl; the substituents R(2), R(3), R(4), R(5) or R(1), R(2), R(4), R(5) or R(1), R(2), R(3), R(5) remaining in each case are independently of one another hydrogen, F, Cl, Br, I, $(C_1-C_8)$-alkyl, $(C_3-C_8)$-alkenyl, $(C_1-C_7)$-perfluoroalkyl, $C_pH_{2p}R(18)$, or up to 2 groups CN, $NO_2$, NR(16)R(17), p is zero or 1, R(18) is $(C_3-C_8)$-cycloalkyl, phenyl, which is unsubstituted or substituted by 1–3 substituents from the group consisting of F, Cl, $CF_3$, methyl, methoxy and NR(19)R(20), R(19) and R(20) are hydrogen, $CH_3$, R(16) is hydrogen, $(C_1-C_8)$-alkyl, $(C_1-C_8)$-perfluoroalkyl, $(C_3-C_8)$-alkenyl, —$C_qH_{2q}$—R(21), q is zero or 1, R(21) is $(C_3-C_8)$-cycloalkyl, phenyl, which is unsubstituted or substituted by 1–3 substituents from the group consisting of F, Cl, $CF_3$, methyl, methoxy and NR(22)R(23), R(22) and R(23) are hydrogen, $CH_3$, R(17) is hydrogen, $(C_1-C_8)$-alkyl, $(C_1-C_8)$-perfluoroalkyl, $(C_3-C_8)$-alkenyl, —$C_rH_{2r}$—R(24), r is zero or 1, R(24) is $(C_3-C_8)$-cycloalkyl, phenyl, which is unsubstituted or substituted by 1–3 substituents from the group consisting of F, Cl, $CF_3$, methyl, methoxy and NR(25)R(26), R(25) and R(26) are hydrogen or $CH_3$, where R(16) and R(17) can also together be 4 or 5 methylene groups, of which one $CH_2$ group can be replaced by oxygen, S, NH, N—$CH_3$ or N-benzyl.

Compounds of the formula I are particularly preferred in which:

R(1), R(3) or R(4) is —NR(6) C=X NR(7)R(8),

X is oxygen, S,

R(6) is hydrogen, $(C_1-C_4)$-alkyl, $(C_1-C_4)$-perfluoroalkyl,

R(7) is hydrogen, $(C_1-C_4)$-alkyl, $(C_1-C_4)$-perfluoroalkyl, $(C_3-C_8)$-alkenyl, —$C_oH_{2o}$—R(12), o is zero or 1, R(12) is $(C_3-C_8)$-cycloalkyl, phenyl, which is unsubstituted or substituted by 1–3 substituents from the group consisting of F, Cl, $CF_3$, methyl, methoxy and NR(13)R(14), R(13) and R(14) are H, $CH_3$, R(8) is defined as R(7), where R(7) and R(8) can also together be 4 or 5 methylene groups, of which one $CH_2$ group can be replaced by oxygen, S, NH, N—$CH_3$ or N-benzyl;

the substituents R(2), R(3), R(4), R(5) or R(1), R(2), R(4), R(5) or R(1), R(2), R(3), R(5) remaining in each case are independently of one another hydrogen, F, Cl, Br, I, $(C_1-C_4)$-alkyl, $(C_1-C_4)$-perfluoroalkyl, $C_pH_{2p}$R(18), or up to 2 groups CN, $NO_2$, NR(16)R(17), p is zero or 1, R(18) is $(C_3-C_8)$-cycloalkyl, phenyl, which is unsubstituted or substituted by 1–3 substituents from the group consisting of F, Cl, $CF_3$, methyl, methoxy and NR(19)R(20), R(19) and R(20) are hydrogen, $CH_3$, R(16) is hydrogen, $(C_1-C_4)$-alkyl, $(C_1-C_4)$-perfluoroalkyl, R(17) is hydrogen, $(C_1-C_4)$-alkyl, $(C_1-C_4)$-perfluoroalkyl, $(C_3-C_8)$-alkenyl, —$C_rH_{2r}$—R(24), r is zero or 1, R(24) is $(C_3-C_8)$-cycloalkyl, phenyl, which is unsubstituted or substituted by 1–3 substituents from the group consisting of F, Cl, $CF_3$, methyl, methoxy and NR(25)R(26), R(25) and R(26) are hydrogen or $CH_3$, where R(16) and R(17) can also together be 4 or 5 methylene groups, of which one $CH_2$ group can be replaced by oxygen, S, NH, N—$CH_3$ or N-benzyl, and their pharmaceutically tolerated salts.

If one of the substituents R(1) to R(5) contains one or more centers of asymmetry, these centers can have either S- or R-configuration. The compounds can be present as optical isomers, as diastereomers, as racemates or as mixtures thereof.

The designated alkyl radicals can be either straight-chain or branched.

The invention furthermore relates to a process for preparing the compound I, which comprises reacting a compound of the formula II

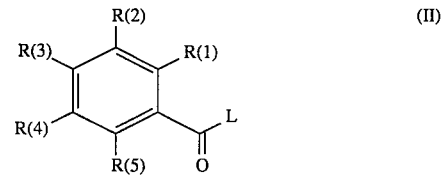

where R(1) to R(5) have the given meaning and L is a leaving group which can readily be substituted nucleophilically, with guanidine.

The activated acid derivatives of the formula II, in which L is an alkoxy, preferably methoxy, group, a phenoxy group, a phenylthio, methylthio or 2-pyridylthio group, or a nitrogen heterocycle, preferably 1-imidazolyl, are advantageously obtained, in a manner known per se, from the underlying carbonyl chlorides (formula II, L=Cl), which, for their part, can in turn be prepared, in a manner known per se, from the underlying carboxylic acids (formula II, L=OH), for example using thionyl chloride.

In addition to the carbonyl chlorides of the formula II (L=Cl), further activated acid derivatives of the formula II can also be prepared, in a manner known per se, directly from the underlying benzoic acid derivatives (formula II, L=OH), such as, for example, the methyl esters of the formula II with L=$OCH_3$ by treating with gaseous HCl in methanol, the imidazolides of the formula II by treating with carbonyldiimidazole [L=1-imidazolyl, Staab, Angew. Chem. Int. Ed. Engl. 1, 351–367 (1962)], the mixed anhydrides II with Cl—$COOC_2H_5$ or tosyl chloride in the presence of triethylamine in an inert solvent, as well as the activation of benzoic acids with dicyclohexylcarbodiimide (DCC) or with O-[(cyano(ethoxycarbonyl)methylene)amino]-1,1,3,3-tetramethyluronium tetrafluoroborate ("TOTU") [Proceedings of the 21st European Peptide Symposium, Peptides 1990, Editors E. Giralt and D. Andreu, Escom, Leiden, 1991]. A series of suitable methods for preparing activated carboxylic acid derivatives of the formula II are given, with citation of the source literature, in J. March, Advanced Organic Chemistry, Third Edition (John Wiley & Sons, 1985), p. 350.

The reaction of an activated carboxylic acid derivative of the formula II with guanidine is effected, in a manner known per se, in a protic or aprotic organic solvent which is polar but inert. In this context, methanol, isopropanol or THF have proved to be suitable, at temperatures of from 20° C. up to the boiling temperature of these solvents, for use in the reaction of the methyl benzoates (II, L=OMe) with guanidine. Aprotic, inert solvents, such as THF, dimethoxyethane and dioxane, were advantageously employed in most of the reactions of compounds II with salt-free guanidine. However, water can also be used, while employing a base, such as, for example, NaOH, as solvent in the reaction of II with guanidine.

When L=Cl, an acid-capturing agent, for example in the form of excess guanidine, is advantageously added in order to bind the hydrohalic acid.

Some of the underlying benzoic acid derivatives of the formula II are known and are described in the literature. The unknown compounds of the formula II may be prepared by methods known from the literature. The resulting benzoic acids are reacted to give compounds I according to the invention in accordance with one of the above-described process variants.

The introduction of some substituents in the 3, 4 and 5 positions is achieved by methods known from the literature involving palladium-mediated cross-coupling of aryl halides or aryl triflates with, for example, organostannanes, organoboronic acids or organoboranes or organocopper or organozinc compounds.

Benzoylguanidines I are in general weak bases and are able to bind acid with the formation of salts. Salts of all pharmacologically tolerated acids, for example halides, in particular hydrochlorides, lactates, sulfates, citrates, tartrates, acetates, phosphates, methanesulfonates and p-toluenesulfonates, are suitable acid addition salts.

The compounds I are substituted acylguanidines.

The most prominent representative of the acylguanidines is the pyrazine derivative amiloride, which is used in therapy as a potassium-sparing diuretic agent. Numerous further compounds of the amiloride type are described in the literature, such as, for example, dimethylamiloride or ethylisopropylamiloride.

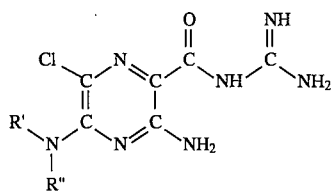

Amiloride: R', R''=H
Dimethylamiloride: R', R''=CH$_3$
Ethylisopropylamiloride: R'=C$_2$H$_5$, R''=CH(CH$_3$)$_2$ In addition to this, investigations have become known which point to antiarrhythmic properties of amiloride (Circulation 79, 1257–1263 (1989)). However, a factor counting against any widespread use of amiloride as an antiarrhythmic agent is that this effect is only weakly expressed and is accompanied by hypotensive and saluretic effects, which latter side effects are undesirable when treating cardiac arrhythmias.

Indications that amiloride has antiarrhythmic properties were also obtained in experiments on isolated animal hearts (Eur. Heart J. 9 (suppl.1): 167 (1988) (book of abstracts)). Thus it was found, using rat hearts, for example, that amiloride was able to completely suppress artificially induced ventricular fibrillation. The above-mentioned amiloride derivative ethylisopropylamiloride was even more potent than amiloride in this model system.

Benzoylguanidines which carry a hydrogen atom in the corresponding position to the radical R(1) are described in the U.S. Pat. No. 5,091,394 (HOE 89/F 288). In the German Patent Application P 42 04 575.4 (HOE 92/F 034, corresponding to the Canadian Laid-Open Patent Application No. 2 089 439, laid open on Aug. 16, 1993), benzoylguanidines are proposed in which, however, the substituents do not have the meanings claimed according to the present invention.

In U.S. Pat. No. 3,780,027, acylguanidines are claimed which are structurally similar to the compounds of the formula I and which are derived from commercially available loop diuretics, such as bumetanide. Correspondingly, these compounds have been reported to have strong salidiuretic activity.

It was surprising, therefore, that the compounds according to the invention do not exhibit any undesirable and disadvantageous salidiuretic properties, but exhibit very good activity against arrhythmias of the type that occur, for example, in association with symptoms of oxygen deficiency. As a consequence of their pharmacological properties, the compounds are outstandingly suitable for use as antiarrhythmic pharmaceuticals having a cardioprotective component for the prophylaxis and treatment of infarction as well as for the treatment of angina pectoris, the compounds also inhibiting or strongly reducing, in a preventive manner, the pathophysiological processes in association with the occurrence of ischemically induced damage, in particular in association with the elicitation of ischemically induced cardiac arrhythmias. On account of their protective effects against pathological hypoxic and ischemic situations, the compounds of the formula I according to the invention can be used, as a result of inhibition of the cellular Na$^+$/H$^+$ exchange mechanism, as pharmaceuticals for treating all acute or chronic damage elicited by ischemia, or diseases which are primarily or secondarily induced thereby. This applies to their use as pharmaceuticals for surgical interventions, e.g. in association with organ transplantations, it being possible to use the compounds to protect the organs in the donor before and during removal and to protect removed organs, for example when being treated with physiological bathing fluids or when being stored in these fluids, and also in association with transfer of the organs into the body of the recipient. The compounds are likewise valuable protective pharmaceuticals for use when carrying out angioplastic surgical interventions, for example on the heart or on peripheral vessels. In accordance with their protective action against ischemically induced damage, the compounds are also suitable for use as pharmaceuticals for treating ischemias of the nervous system, in particular of the CNS, e.g. for the treatment of stroke or of cerebral edema. In addition to this, the compounds of formula I according to the invention are likewise suitable for use in the treatment of forms of shock, such as, for example, allergic, cardiogenic, hypovolemic and bacterial shock.

In addition to this, the compounds of the formula I according to the invention are notable for their strong inhibitory effect on the proliferation of cells, for example the proliferation of fibroblast cells and the proliferation of the smooth muscle cells of the vasculature. For this reason, the compounds of the formula I are suitable, as valuable therapeutic agents, for use in diseases in which cell proliferation represents a primary or secondary cause, and may therefore be used as anti-atherosclerotic agents, and as agents against diabetic secondary complications, carcinomatous disorders, fibrotic disorders, such as pulmonary fibrosis, hepatic fibrosis or renal fibrosis, and against organ hypertrophy and hyperplasia, in particular in hyperplasia or hypertrophy of the prostate.

The compounds according to the invention are efficacious inhibitors of the cellular sodium/proton antiporter (Na$^+$/H$^+$ exchanger), which, in numerous disorders (essential hypertension, atherosclerosis, diabetes, etc.), is also elevated in cells which are readily accessible to measurement, such as, for example, in erythrocytes, blood platelets or leucocytes. The compounds according to the invention are therefore suitable for use as outstanding, simple, scientific tools, for example in their employment as diagnostics for determining and differentiating particular forms of hypertension, but also for use in atherosclerosis, diabetes, proliferative disorders, and so on. In addition, the compounds of the formula I are suitable for use in preventive therapy for preventing the genesis of high blood pressure, for example of essential hypertension.

In comparison with the known compounds, the compounds according to the invention have significantly improved water solubility. They are therefore essentially better suited to i.v. administration.

In this context, pharmaceuticals which contain a compound I can be administered orally, parenterally, intravenously, rectally or by inhalation, the preferred route of administration being dependent on how the disorder manifests itself. In this context, the compounds I may be used alone or together with pharmaceutical auxiliary substances, both in the case of veterinary medicine and in the case of human medicine.

Owing to his specialist knowledge, the person skilled in the art is familiar with which auxiliary substances are suitable for the desired pharmaceutical formulation. In addition to solvents, gel-formers, suppository bases, tablet auxiliary substances, and other active-compound carriers, antioxidants, dispersing agents, emulsifiers, defoamers, taste corrigents, preservatives, solubilizers or dyes, for example, can be used.

In order to prepare a form for oral use, the active compounds are mixed with the additives which are suitable for the purpose, such as excipients, stabilizers or inert diluents, and converted by the customary methods into the forms suitable for administration, such as tablets, coated tablets, hard gelatin capsules or aqueous, alcoholic or oily solutions. Gum arabic, magnesia, magnesium carbonate, potassium phosphate, lactose, glucose or starch, in particular corn starch, for example, can be used as inert excipients. In this context, the preparation can be effected as dry or wet granules. Vegetable or animal oils, for example, such as sunflower oil or cod-liver oil, are suitable for use as oily excipients or as solvents.

For subcutaneous or intravenous administration, the active compounds, if desired together with the substances which are customary for the purpose, such as solubilizers, emulsifiers or additional auxiliary substances, are brought into solution, suspension or emulsion. Examples of suitable solvents are: water, physiological saline solution, or alcohols, for example ethanol, propanol or glycerol, and in addition sugar solutions as well, such as glucose or mannitol solutions, or else a mixture of the different solvents mentioned.

Solutions, suspensions or emulsions of the active compound of the formula I in a pharmaceutically harmless solvent, such as, in particular, ethanol or water, or a mixture of such solvents, are suitable, for example, for use as a pharmaceutical formulation for administration in the form of aerosols or sprays.

Depending on requirements, the formulation can also contain still further pharmaceutical auxiliary substances, such as surface-active agents, emulsifiers and stabilizers, as well as a propellant. Such a preparation customarily contains the active compound in a concentration of about 0.1 to 10, in particular of about 0.3 to 3% by weight.

The dosage of the active compound of the formula I to be administered, and the frequency of the administration, depend on the strength and the duration of the effect of the compounds used; additionally also on the nature and severity of the disease to be treated, as well as on the sex, age, weight and individual responsiveness of the mammal to be treated.

On average, the daily dose of a compound of the formula I for a patient of about 75 kg in weight is at least 0.001 mg/kg, preferably 0.01 mg/kg, up to at most 10 mg/kg, preferably 1 mg/kg, of body weight. In acute episodes of the illness, for example immediately after suffering a cardiac infarction, even higher, and in particular more frequent, dosages may also be necessary, for example up to 4 individual doses per day. In association with i.v. use, in particular, for example in the case of an infarction patient in intensive care, up to 200 mg per day may be necessary.

List of abbreviations:

MeOH methanol
DMF N,N-dimethylformamide
EI electron impact
DCI desorption-chemical ionization
RT room temperature
EA ethyl acetate (EtOAc)
m.p. melting point
HEP n-heptane
DME dimethoxyethane
ES electron spray
FAB fast atom bombardment
$CH_2Cl_2$ dichloromethane
THF tetrahydrofuran
eq. equivalent
in vac. in vacuo
Experimental part General directions for preparing benzoic acids substituted by urea in position 2 from isatoic anhydrides:

Variant 1 A: From isatoic anhydrides and a silylated amine 1.1 eq. of a trimethylsilylated amine were added to 1.0 eq. of the isatoic anhydride in $CH_2Cl_2$ (2 ml/mmol) and the mixture was stirred at a suitable temperature (RT to reflux). After removal of the solvent in vac., water was added (1.5 ml/mmol). The benzoic acid derivative which crystallized out was filtered off, washed with water and dried in vac..

Variant 1 B: From N-silylated isatoic anhydrides and an amine 1.05 eq. of trimethylsilyl chloride were added at RT to 1.0 eq. of the isatoic anhydride and 1.0 eq. of triethylamine in $CH_2Cl_2$ or $CHCl_3$ (2 ml/mmol) and the mixture was stirred for a suitable time. 1.0 eq. of the amine was subsequently added and the mixture was stirred at a suitable temperature (RT to reflux). Working up was carried out analogously to variant 1 A.

General instructions for preparing benzoylguanidines (I)
Variant 2 A: from benzoic acids (II, L=OH)

1.0 eq. of the benzoic acid derivative of the formula II is dissolved or suspended in anhydrous THF (5 ml/mmol) and 1.1 eq. of carbonyldiimidazole are then added. After stirring at RT for 2 hours, 5.0 eq. of guanidine are introduced into the reaction solution. After stirring overnight, the THF is distilled off under reduced pressure in a rotary evaporator, water is added to the mixture, which is then adjusted to pH 6 to 7 using 2N HCl, and the corresponding benzoylguanidine (formula I) is filtered off. The benzoylguanidines thus obtained can be converted into the corresponding salts by treatment with aqueous, methanolic or ethereal hydrochloric acid or other pharmacologically tolerated acids.

Variant 2 B: from alkyl benzoates (II, L=O-alkyl)

1.0 eq. of the alkyl benzoate of the formula II and 5.0 eq. of guanidine (free base) are dissolved in isopropanol or suspended in THF and heated under reflux (typical reaction time 2 to 5 hours) until conversion is complete (thin-layer checking). The solvent is distilled off under reduced pressure in a rotary evaporator, and the residue is taken up in EA and washed 3×with $NaHCO_3$ solution. Drying takes place over $Na_2SO_4$, the solvent is distilled off in vacuo, and the residue is chromatographed on silica gel using a suitable eluent, e.g. EA/MeOH 5:1.

(Salt formation: compare variant A)

General directions for preparing urea- and thiourea-substituted benzoic acid esters from aminobenzoic acid esters and iso- or isothiocyanates Variant 3:

1.0 eq. of the aminobenzoic acid ester was treated in toluene (2 ml/mmol) and pyridine (4 eq.) with iso- or isothiocyanate and stirred at 80° C. After reaction was complete (1–6 h), the cooled solution was treated with water and rendered acidic with 2N hydrochloric acid. The organic phase was separated off, the aqueous phase was extracted twice by shaking with EA, and the organic phases were dried and concentrated in vac.. The solid which remained was washed with ether and dried in vac..

EXAMPLE 1: 5-Chloro-2-(piperidinocarbonylamino)benzoylguanidine was prepared from 5-chloroisatoic anhydride and N-trimethylsilylpiperidine in accordance with variants 1 A and 2 A.

(Benzoic acid intermediate: colorless crystals, m.p. 165° C.)

Colorless crystals, m.p. 151° C.

EXAMPLE 2: 2-(Piperidinocarbonylamino)benzoylguanidine was prepared from isatoic anhydride and N-trimethylsilylpiperidine in accordance with variants 1 A and 2 A.

(Benzoic acid intermediate: colorless crystals, m.p. 136° C.)

Colorless crystals, m.p. 158° C.

EXAMPLE 3: 5-Chloro-2-(dimethylaminocarbonylamino)benzoylguanidine hydrochloride was prepared from 5-chloroisatoic anhydride and N,N-dimethyl-N-trimethylsilylamine in accordance with variants 1 A and 2 A.

(Benzoic acid intermediate: colorless crystals, m.p. 177° C.)

Colorless crystals, m.p. 174° C.

EXAMPLE 4: 5-Chloro-2-(morpholinocarbonylamino)benzoylguanidine hydrochloride was prepared from 5-chloroisatoic anhydride and N-trimethylsilylmorpholine in accordance with variants 1 A and 2 A.

(Benzoic acid intermediate: colorless crystals, m.p. 187° C.)

Colorless crystals, m.p. 162° C.

EXAMPLE 5: 5-Chloro-2-(4-methylpiperazin-1-yl-carbonylamino)benzoylguanidine dihydrochloride was prepared from 5-chloroisatoic anhydride and 4-N-methylpiperazine in accordance with variants 1 B and 2 A.

(Benzoic acid intermediate: colorless crystals, m.p. 207° C.)

Colorless crystals, m.p. 163° C.

EXAMPLE 6: 5-Chloro-2-(pyrrolidin-1-yl-carbonylamino)benzoylguanidine hydrochloride was prepared from 5-chloroisatoic anhydride and N-trimethylsilylpyrrolidine in accordance with variants 1 A and 2 A.

(Benzoic acid intermediate: colorless crystals, m.p. 193° C.)

Colorless crystals, m.p. 164° C.

EXAMPLE 7: 5-Chloro-2-(tert-butylaminocarbonylamino)benzoylguanidine hydrochloride was prepared from 5-chloroisatoic anhydride and N-trimethylsilyl-tert-butylamine in accordance with variants 1 A and 2 A.

(Benzoic acid intermediate: colorless crystals, m.p. 155° C.)

Colorless crystals, m.p. 145° C.

EXAMPLE 8: 3-(n-Propylaminocarbonylamino)benzoylguanidine hydrochloride was prepared from methyl 3-aminobenzoate and n-propyl isocyanate in accordance with variants 3 and 2 B.

(Benzoic acid ester intermediate: colorless crystals, m.p. 140° C.)

Colorless crystals, m.p. 142° C.

EXAMPLE 9: 3-(Phenylaminocarbonylamino)benzoylguanidine hydrochloride was prepared from methyl 3-aminobenzoate and phenyl isocyanate in accordance with variants 3 and 2 B.

(Benzoic acid ester intermediate: colorless crystals, m.p. 159° C.)

Colorless crystals, m.p. 182° C.

EXAMPLE 10: 3-(Cyclohexylaminocarbonylamino)benzoylguanidine hydrochloride was prepared from methyl 3-aminobenzoate and cyclohexyl isocyanate in accordance with variants 3 and 2 B.

(Benzoic acid ester intermediate: colorless crystals, m.p. 122° C.)

Amorphous solid.

EXAMPLE 11: 3-(Ethylaminothiocarbonylamino)benzoylguanidine hydrochloride was prepared from methyl 3-aminobenzoate and ethyl isothiocyanate in accordance with variants 3 and 2 B.

(Benzoic acid ester intermediate: colorless crystals, m.p. 130° C.)

Colorless crystals, m.p. 130° C.

EXAMPLE 12: 3-(Phenylaminothiocarbonylamino)benzoylguanidine hydrochloride was prepared from methyl 3-aminobenzoate and phenyl isothiocyanate in accordance with variants 3 and 2 B.

(Benzoic acid ester intermediate: colorless crystals, m.p. 130° C.)

Colorless crystals, m.p. 145° C.

EXAMPLE 13: 3-(Cyclohexylaminothiocarbonylamino)benzoylguanidine hydrochloride was prepared from methyl 3-aminobenzoate and cyclohexyl isothiocyanate in accordance with variants 3 and 2 B.

(Benzoic acid ester intermediate: colorless crystals, m.p. 115° C.)

Colorless crystals, m.p. 158° C.

EXAMPLE 14: 4-Chloro-3-(n-propylaminocarbonylamino)benzoylguanidine hydrochloride was prepared from methyl 4-chloro-3-aminobenzoate and n-propyl isocyanate in accordance with variants 3 and 2 B.

(Benzoic acid ester intermediate: colorless crystals, m.p. 140° C.)

Colorless crystals, m.p. 230° C.

EXAMPLE 15: 4-Chloro-3-(phenylaminocarbonylamino)benzoylguanidine hydrochloride was prepared from methyl 4-chloro-3-aminobenzoate and phenyl isocyanate in accordance with variants 3 and 2 B.

(Benzoic acid ester intermediate: colorless crystals, m.p. 186° C.)

Colorless crystals, m.p. 232° C.

EXAMPLE 16: 4-Chloro-3-(cyclohexylaminocarbonylamino)benzoylguanidine hydrochloride was prepared from methyl 4-chloro-3-aminobenzoate and cyclohexyl isocyanate in accordance with variants 3 and 2 B.

(Benzoic acid ester intermediate: colorless crystals, m.p. 158° C.)

Colorless crystals, m.p. 223° C.

EXAMPLE 17: 4-Chloro-3-(ethylaminothiocarbonylamino)benzoylguanidine hydrochloride was prepared from methyl 4-chloro-3-aminobenzoate and ethyl isothiocyanate in accordance with variants 3 and 2 B.

(Benzoic acid ester intermediate: colorless crystals, m.p. 152° C.)

Colorless crystals, m.p. 145° C.

EXAMPLE 18: 4-Chloro-3-(phenylaminothiocarbonylamino)benzoylguanidine hydrochloride was prepared from methyl 4-chloro-3-aminobenzoate and phenyl isothiocyanate in accordance with variants 3 and 2 B.

(Benzoic acid ester intermediate: colorless crystals, m.p. 130° C.)

Colorless crystals, m.p. 145° C.

EXAMPLE 19: 4-Chloro-3-(cyclohexylaminothiocarbonylamino)benzoylguanidine hydrochloride was prepared from methyl 4-chloro-3-aminobenzoate and cyclohexyl isothiocyanate in accordance with variants 3 and 2 B.

Colorless crystals, m.p. 190° C.

EXAMPLE 20: 3,5-Dichloro-4-(n-propylaminocarbonylamino)benzoylguanidine hydrochloride was prepared from methyl 3,5-dichloro-4-aminobenzoate and n-propyl isocyanate in accordance with variants 3 and 2 B.

(Benzoic acid ester intermediate: colorless oil)

Colorless crystals, m.p. 220° C.

EXAMPLE 21: 3,5-Dichloro-4-(phenylaminocarbonylamino)benzoylguanidine hydrochloride was prepared from methyl 3,5-dichloro-4-aminobenzoate and phenyl isocyanate in accordance with variants 3 and 2 B.

(Benzoic acid ester intermediate: colorless crystals, m.p. 82° C.)

Colorless crystals, m.p. 234° C.

Pharmacological data:

Inhibition of the $Na^+/H^+$ exchanger of rabbit erythrocytes:

New Zealand White rabbits (Ivanovas) received a standard diet containing 2% cholesterol for six weeks in order to activate the $Na^+/H^+$ exchange and thus to be able to determine, by flame photometry, the $Na^+$ influx into the erythrocytes via $Na^+/H^+$ exchange. The blood was removed from the aural arteries and rendered incoagulable using 25 IE/ml of potassium heparin. A part of each sample was used for the duplicate determination of the hematocrit by means of centrifugation. Aliquots of in each case 100 µl were used for measuring the initial $Na^+$ content of the erythrocytes.

In order to determine the amiloride-sensitive sodium influx, 100 µl of each blood sample were in each case incubated, at pH 7.4 and 37° C., in 5 ml of a hyperosmolar salt/sucrose medium (mmol/l: 140 NaCl, 3 KCl, 150 sucrose, 0.1 ouabain, 20 tris(hydroxymethyl)aminomethane). The erythrocytes were then washed three times with ice-cold $MgCl_2$/ouabain solution (mmol/l: 112 $MgCl_2$, 0.1 ouabain) and hemolyzed in 2.0 ml of distilled water. The intracellular sodium content was determined by flame photometry.

The net influx of $Na^+$ was calculated from the difference between the initial sodium values and the sodium content of the erythrocytes following incubation. The amiloride-inhibitable sodium influx resulted from the difference in the sodium content of the erythrocytes following incubation with and without amiloride $3 \times 10^{-4}$ mol/l. This method was also employed in the case of the compounds according to the invention.

Results of inhibition of the $Na^+/H^+$ exchanger:

| Example | $IC_{50}$ (µmol) |
|---------|------------------|
| 1 | 1–2 |
| 3 | 3 |
| 7 | 3–8 |
| 17 | 3–5 |
| 20 | 2–5 |
| 21 | 1 |

We claim:

1. A benzoylguanidine of the formula I

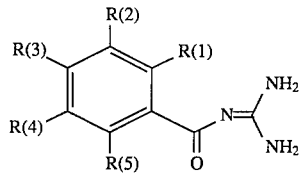

in which:

R(1), R(3) or R(4) is —NR(6) C=X NR(7)R(8),

X is oxygen, S,

R(6) is hydrogen, $(C_1-C_8)$-alkyl, $(C_1-C_8)$-perfluoroalkyl, $(C_3-C_8)$-alkenyl, —$C_nH_{2n}$—R(9), n is zero, 1, 2, 3 or 4, R(9) is $(C_3-C_8)$-cycloalkyl, phenyl, biphenylyl or naphthyl, where the aromatic systems are unsubstituted or substituted by 1–3 substituents from the group consisting of F, Cl, $CF_3$, methyl, methoxy and NR(10) R(11), R(10) and R(11) are H, $(C_1-C_4)$-alkyl or $(C_1-C_4)$-perfluoroalkyl;

R(7) is hydrogen, $(C_1-C_8)$-alkyl, $(C_1-C_8)$-perfluoroalkyl, $(C_3-C_8)$-alkenyl, —$C_oH_{2o}$—R(12), o is zero, 1, 2, 3 or 4, R(12) is $(C_3-C_8)$-cycloalkyl, phenyl, biphenylyl or naphthyl, where the aromatic systems are unsubstituted or substituted by 1–3 substituents from the group consisting of F, Cl, $CF_3$, methyl, methoxy and NR(13)R(14), R(13) and R(14) are H, $(C_1-C_4)$-alkyl or $(C_1-C_4)$-perfluoroalkyl;

R(8) is defined as R(7);

where R(7) and R(8) can also together be 4 or 5 methylene groups, of which one $CH_2$ group can be replaced by oxygen, S, NH, N—$CH_3$ or N-benzyl;

the substituents R(2), R(3), R(4), R(5) or R(1), R(2), R(4), R(5) or R(1), R(2), R(3), R(5) remaining in each case are independently of one another hydrogen, F, Cl, Br, I, —$O_{ta}(C_1-C_8)$-alkyl, —$O_{tb}(C_3-C_8)$-alkenyl, —$O_{tc}(CH_2)_bC_dF_{2d+1}$, —$O_{td}C_pH_{2p}R(18)$, or up to 2 groups CN, $NO_2$, NR(16)R(17), b is zero or 1, d is 1, 2, 3, 4, 5, 6 or 7, ta is zero or 1, tb is zero or 1, tc is zero or 1, td is zero or 1, p is zero, 1, 2, 3 or 4, R(18) is $(C_3-C_8)$-cycloalkyl, phenyl, biphenylyl or naphthyl, where the aromatic systems are unsubstituted or substituted by 1–3 substituents from the group consisting of F, Cl, $CF_3$, methyl, methoxy and NR(19)R(20), R(19) and R(20) are hydrogen, $(C_1-C_4)$-alkyl, $(C_1-C_4)$-perfluoroalkyl, R(16) is hydrogen, $(C_1-C_8)$-alkyl, $(C_1-C_8)$-perfluoroalkyl, $(C_3-C_8)$-alkenyl, —$C_qH_{2q}$—R(21), q is zero, 1, 2, 3 or 4, R(21) is $(C_3-C_8)$-cycloalkyl, phenyl, biphenylyl or naphthyl, where the aromatic systems are unsubstituted or substituted by 1–3 substituents from the group consisting of F, Cl, $CF_3$, methyl, methoxy and NR(22)R(23), R(22) and R(23) are hydrogen, $(C_1-C_4)$-alkyl or $(C_1-C_4)$-perfluoroalkyl, R(17) is hydrogen, $(C_1-C_8)$-alkyl, $(C_1-C_8)$-perfluoroalkyl, $(C_3-C_8)$-alkenyl, $—C_rH_{2r}—R(24)$, r is zero, 1, 2, 3 or 4, R(24) is $(C_3-C_8)$-cycloalkyl, phenyl, biphenylyl or naphthyl, where the aromatic systems are unsubstituted or substituted by 1–3 substituents from the group consisting of F, Cl, $CF_3$, methyl, methoxy and NR(25) R(26), R(25) and R(26) are hydrogen, $(C_1-C_4)$-alkyl or $(C_1-C_4)$-perfluoroalkyl;

where R(16) and R(17) can also together be 4 or 5 methylene groups, of which one $CH_2$ group can be replaced by oxygen, S, NH, N—$CH_3$ or N-benzyl, as well as pharmaceutically tolerated salts thereof.

2. A compound of the formula I as claimed in claim 1, wherein:

R(1), R(3) or R(4) is —NR(6) C=X NR(7)R(8),

X is oxygen, S,

R(6) is hydrogen, $(C_1-C_8)$-alkyl, $(C_1-C_8)$-perfluoroalkyl, $(C_3-C_8)$-alkenyl, $—C_nH_{2n}—R(9)$, n is zero or 1, R(9) is $(C_3-C_8)$-cycloalkyl, phenyl, which is unsubstituted or substituted by 1–3 substituents from the group consisting of F, Cl, $CF_3$, methyl, methoxy and NR(10) R(11), R(10) and R(11) are H, $CH_3$, R(7) is hydrogen, $(C_1-C_8)$-alkyl, $(C_1-C_8)$-perfluoroalkyl, $(C_3-C_8)$-alkenyl, $—C_oH_{2o}—R(12)$, o is zero or 1, R(12) is $(C_3-C_8)$-cycloalkyl, phenyl, which is unsubstituted or substituted by 1–3 substituents from the group consisting of F, Cl, $CF_3$, methyl, methoxy and NR(13) R(14), R(13) and R(14) are H, $CH_3$, R(8) is defined as R(7), where R(7) and R(8) can also together be 4 or 5 methylene groups, of which one $CH_2$ group can be replaced by oxygen, S, NH, N—$CH_3$ or N-benzyl;

the substituents R(2), R(3), R(4), R(5) or R(1), R(2), R(4), R(5) or R(1), R(2), R(3), R(5) remaining in each case are independently of one another hydrogen, F, Cl, Br, I, $(C_1-C_8)$-alkyl, $(C_3-C_8)$alkenyl, $(C_1-C_7)$-perfluoroalkyl, $C_pH_{2p}R(18)$, or up to 2 groups CN, $NO_2$, NR(16)R(17), p is zero or 1, R(18) is $(C_3-C_8)$-cycloalkyl, phenyl, which is unsubstituted or substituted by 1–3 substituents from the group consisting of F, Cl, $CF_3$, methyl, methoxy and NR(19)R(20), R(19) and R(20) are hydrogen, $CH_3$, R(16) is hydrogen, $(C_1-C_8)$-alkyl, $(C_1-C_8)$-perfluoroalkyl, $(C_3-C_8)$-alkenyl, $—C_qH_{2q}—R(21)$, q is zero or 1, R(21) is $(C_3-C_8)$-cycloalkyl, phenyl, which is unsubstituted or substituted by 1–3 substituents from the group consisting of F, Cl, $CF_3$, methyl, methoxy and NR(22) R(23), R(22) and R(23) are hydrogen, $CH_3$, R(17) is hydrogen, $(C_1-C_8)$-alkyl, $(C_1-C_8)$-perfluoroalkyl, $(C_3-C_8)$-alkenyl, $—C_rH_{2r}—R(24)$, r is zero or 1, R(24) is $(C_3-C_8)$-cycloalkyl, phenyl, which is unsubstituted or substituted by 1–3 substituents from the group consisting of F, Cl, $CF_3$, methyl, methoxy and NR(25) R(26), R(25) and R(26) are hydrogen or $CH_3$, where R(16) and R(17) can also together be 4 or 5 methylene groups, of which one $CH_2$ group can be replaced by oxygen, S, NH, N—$CH_3$ or N-benzyl, as well as pharmaceutically tolerated salts thereof.

3. A compound of the formula I as claimed in claim 1, wherein:

R(1), R(3) or R(4) is —NR(6) C=X NR(7)R(8),

X is oxygen, S,

R(6) is hydrogen, $(C_1-C_4)$-alkyl, $(C_1-C_4)$-perfluoroalkyl,

R(7) is hydrogen, $(C_1-C_4)$-alkyl, $(C_1-C_4)$-perfluoroalkyl, $(C_3-C_8)$-alkenyl, $—C_oH_{2o}—R(12)$, o is zero or 1, R(12) is $(C_3-C_8)$-cycloalkyl, phenyl, which is unsubstituted or substituted by 1–3 substituents from the group consisting of F, Cl, $CF_3$, methyl, methoxy and NR(13) R(14), R(13) and R(14) are H, $CH_3$, R(8) is defined as R(7), where R(7) and R(8) can also together be 4 or 5 methylene groups, of which one $CH_2$ group can be replaced by oxygen, S, NH, N—$CH_3$ or N-benzyl;

the substituents R(2), R(3), R(4), R(5) or R(1), R(2), R(4), R(5) or R(1), R(2), R(3), R(5) remaining in each case are independently of one another hydrogen, F, Cl, Br, I, $(C_1-C_4)$-alkyl, $(C_1-C_4)$-perfluoroalkyl, $C_pH_{2p}R(18)$, or up to 2 groups CN, $NO_2$, NR(16)R(17), p is zero or 1, R(18) is $(C_3-C_8)$-cycloalkyl, phenyl, which is unsubstituted or substituted by 1–3 substituents from the group consisting of F, Cl, $CF_3$, methyl, methoxy and NR(19)R(20), R(19) and R(20) are hydrogen, $CH_3$, R(16) is hydrogen, $(C_1-C_4)$-alkyl, $(C_1-C_4)$-perfluoroalkyl, R(17) is hydrogen, $(C_1-C_4)$-alkyl, $(C_1-C_4)$-perfluoroalkyl, $(C_3-C_8)$-alkenyl, $—C_rH_{2r}—R(24)$, r is zero or 1, R(24) is $(C_3-C_8)$-cycloalkyl, phenyl, which is unsubstituted or substituted by 1–3 substituents from the group consisting of F, Cl, $CF_3$, methyl, methoxy and NR(25)R(26), R(25) and R(26) are hydrogen or $CH_3$, where R(16) and R(17) can also together be 4 or 5 methylene groups, of which one $CH_2$ group can be replaced by oxygen, S, NH, N—$CH_3$ or N-benzyl, as well as pharmaceutically tolerated salts thereof.

4. A method of treating arrhythmias, which comprises administering to a host in need of said treatment an effective amount of a compound of the formula I as claimed in claim 1.

5. A pharmaceutical composition for the treatment of arrhythmias, which comprises a compound of formula I as claimed in claim 1 together with a pharmaceutically acceptable auxiliary substance.

6. A method for treating or preventing cardiac infarct, which comprises administering to a host in need of said treatment an effective amount of a compound of the formula I as claimed in claim 1.

7. A method of treating or preventing angina pectoris, which comprises administering to a host in need of said treatment an effective amount of a compound of the formula I as claimed in claim 1.

8. A method of treating or preventing ischemic conditions of the heart, which comprises administering to a host in need of said treatment an effective amount of a compound of the formula I as claimed in claim 1.

9. A method of treating or preventing ischemic conditions of the peripheral and central nervous systems and of stroke, which comprises administering to a host in need of said treatment an effective amount of a compound of the formula I as claimed in claim 1.

10. A method of treating or preventing ischemic conditions of the peripheral organs and limbs, which comprises administering to a host in need of said treatment an effective amount of a compound of the formula I as claimed in claim 1.

11. A method of treating shock conditions, which comprises administering to a host in need of said treatment an effective amount of a compound of the formula I as claimed in claim 1.

12. A pharmaceutical composition for use in surgical operations and organ transplants, which comprises an effective amount of a compound of formula I as claimed in claim 1 and a pharmaceutically acceptable auxiliary substance.

13. A pharmaceutical composition for use in preserving and storing transplants for surgical procedures, which comprises an effective amount of a compound of formula I as claimed in claim 1.

14. A method of treating diseases in which cell proliferation is a primary or secondary cause, which comprises administering to a host in need of said treatment an effective amount of a compound of the formula I as claimed in claim 1.

15. The method according to claim 14, wherein the disease in which cell proliferation is a primary or secondary cause, is atherosclerosis, a secondary complication of diabetes, cancer, a fibrotic disorder or prostate hyperplasia.

16. The method according to claim 15, wherein the fibrotic disorder is pulmonary fibrosis, hepatic fibrosis, or renal fibrosis.

17. A diagnostic aid for inhibiting the Na+/H+ exchanger and for diagnosing hypertension and proliferative diseases, which comprises an effective amount of a compound of formula I as claimed in claim 1.

18. A pharmaceutical composition for the treatment of cardiac infarct, angina pectoris, ischemic conditions of the heart, the peripheral and central nervous systems, the peripheral organs and, limbs, of stroke, of shock conditions, and of diseases in which cell proliferation is a primary or secondary cause, which comprises an effective amount of a compound of formula I as claimed in claim 1 together with a pharmaceutically acceptable auxiliary substance.

19. A process for preparing a compound I as claimed in claim 1, which comprises reacting
a compound of the formula II

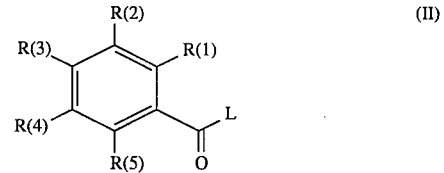

in which R(1) to R(5) have the abovementioned meaning and L is a leaving group which can readily be substituted nucleophilically, with guanidine.

* * * * *